(12) United States Patent
Carbunaru et al.

(10) Patent No.: US 8,224,449 B2
(45) Date of Patent: Jul. 17, 2012

(54) MICROSTIMULATOR WITH FLAP ELECTRODES

(75) Inventors: Rafael Carbunaru, Valley Village, CA (US); Andrew DiGiore, Santa Monica, CA (US); Brett Schleicher, Valencia, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 386 days.

(21) Appl. No.: 12/493,928

(22) Filed: Jun. 29, 2009

(65) Prior Publication Data

US 2010/0331933 A1    Dec. 30, 2010

(51) Int. Cl.
*A61N 1/02* (2006.01)
(52) U.S. Cl. ............ 607/36; 607/115; 607/118
(58) Field of Classification Search .......... 607/36, 607/37, 115, 117, 118
See application file for complete search history.

(56) References Cited

U.S. PATENT DOCUMENTS

| | | | |
|---|---|---|---|
| 3,683,933 A * | 8/1972 | Mansfield | 607/36 |
| 4,481,953 A | 11/1984 | Gold et al. | |
| 4,573,481 A | 3/1986 | Bullara | |
| 4,690,148 A | 9/1987 | Hess | |
| 4,934,368 A * | 6/1990 | Lynch | 607/2 |
| 4,940,065 A | 7/1990 | Tanagho et al. | |
| 5,005,587 A | 4/1991 | Scott | |
| 5,016,808 A | 5/1991 | Heil, Jr. et al. | |
| 5,188,104 A | 2/1993 | Wernicke et al. | |
| 5,215,086 A | 6/1993 | Terry, Jr. et al. | |
| 5,215,089 A | 6/1993 | Baker, Jr. | |
| 5,231,988 A | 8/1993 | Wernicke et al. | |
| 5,251,634 A | 10/1993 | Weinberg | |
| 5,269,303 A | 12/1993 | Wernicke et al. | |
| 5,299,569 A | 4/1994 | Wernicke et al. | |
| 5,318,591 A | 6/1994 | Causey, III et al. | |
| 5,330,515 A | 7/1994 | Rutecki et al. | |
| 5,335,657 A | 8/1994 | Terry, Jr. et al. | |
| 5,531,778 A | 7/1996 | Maschino et al. | |
| 5,540,730 A | 7/1996 | Terry, Jr. et al. | |
| 5,555,618 A | 9/1996 | Winkler | |
| 5,571,150 A | 11/1996 | Wernicke et al. | |
| 5,707,400 A | 1/1998 | Terry, Jr. et al. | |
| 5,728,149 A | 3/1998 | Laske et al. | |
| 5,792,188 A | 8/1998 | Starkweather et al. | |
| 5,836,971 A | 11/1998 | Starkweather | |
| 6,010,500 A | 1/2000 | Sherman et al. | |
| 6,090,104 A | 7/2000 | Webster, Jr. | |

(Continued)

FOREIGN PATENT DOCUMENTS

WO    WO 93/01862 A1    2/1993

(Continued)

*Primary Examiner* — Brian T Gedeon
(74) *Attorney, Agent, or Firm* — Vista IP Law Group LLP

(57) ABSTRACT

An implantable microstimulator includes an elongate casing, a flap coupled directly to the casing, and electrodes attached to the flap such that the electrodes extend laterally relative to the longitudinal axis of the casing. The electrodes are coupled to active circuitry that is housed within the casing. Due to the lateral arrangement of the electrodes relative to the casing, effective operation of the microstimulator may still occur even after the microstimulator migrates away from the target stimulation site. Since there are not any leads associated with the microstimulator, the entire microstimulator, including the electrodes and the casing, is implanted adjacent to the target stimulation site. The electrodes may be configured for monopolar or multi-polar stimulation. In one example, the microstimulator includes an insulative coating on the casing and the coating and the flap are contiguous.

19 Claims, 20 Drawing Sheets

U.S. PATENT DOCUMENTS

| | | |
|---|---|---|
| 6,205,359 B1 | 3/2001 | Boveja |
| 6,208,902 B1 | 3/2001 | Boveja |
| 6,269,270 B1 | 7/2001 | Boveja |
| 6,296,639 B1 | 10/2001 | Truckai et al. |
| 6,440,059 B1 | 8/2002 | Haas et al. |
| 6,589,237 B2 | 7/2003 | Woloszko et al. |
| 6,600,956 B2 | 7/2003 | Maschino et al. |
| 6,615,695 B1 | 9/2003 | Hjelle et al. |
| 6,905,495 B1 | 6/2005 | Fuimaono et al. |
| 6,917,834 B2 | 7/2005 | Koblish et al. |
| 7,054,692 B1 | 5/2006 | Whitehurst et al. |
| 7,158,832 B2 | 1/2007 | Kieval et al. |
| 7,203,548 B2 * | 4/2007 | Whitehurst et al. ............ 607/39 |
| 7,480,532 B2 | 1/2009 | Kieval et al. |
| 7,499,747 B2 | 3/2009 | Kieval et al. |
| 7,502,650 B2 | 3/2009 | Kieval |
| 7,551,964 B2 | 6/2009 | Dobak, III |
| 2004/0111139 A1 | 6/2004 | McCreery |
| 2005/0033136 A1 | 2/2005 | Govari |
| 2005/0070974 A1 | 3/2005 | Knudson |
| 2005/0131467 A1 | 6/2005 | Boveja |
| 2006/0004417 A1 | 1/2006 | Rossing |
| 2006/0041277 A1 | 2/2006 | Deem |
| 2006/0259077 A1 | 11/2006 | Pardo |
| 2006/0265026 A1 | 11/2006 | Madjar |
| 2006/0293721 A1 | 12/2006 | Tarver |
| 2007/0100406 A1 | 5/2007 | Kollatschny |
| 2007/0112404 A1 | 5/2007 | Mann |
| 2007/0288076 A1 | 12/2007 | Bulkes |
| 2008/0058887 A1 | 3/2008 | Griffin |
| 2008/0161865 A1 | 7/2008 | Hagen |
| 2008/0262411 A1 | 10/2008 | Dobak, III |
| 2008/0319504 A1 | 12/2008 | Loushin |
| 2009/0030493 A1 | 1/2009 | Colborn |
| 2009/0112292 A1 | 4/2009 | Armstrong |
| 2009/0118777 A1 | 5/2009 | Iki |
| 2009/0125079 A1 | 5/2009 | Armstrong |

FOREIGN PATENT DOCUMENTS

| | | |
|---|---|---|
| WO | WO 93/02744 A1 | 2/1993 |
| WO | WO 94/00185 A1 | 1/1994 |

\* cited by examiner

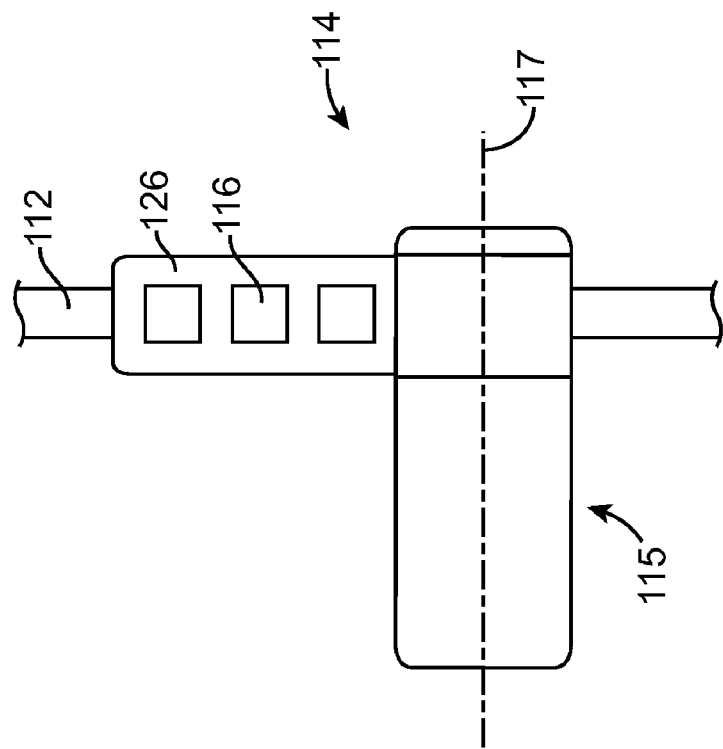
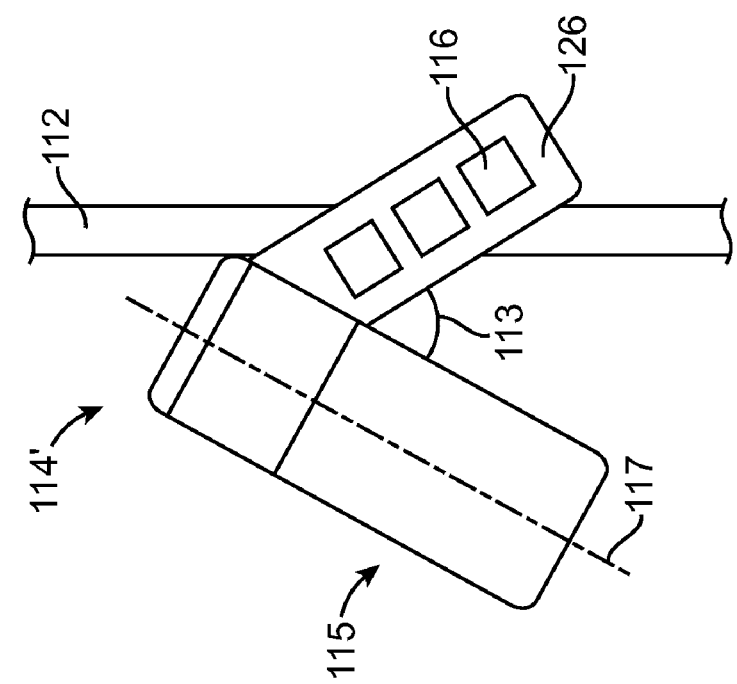

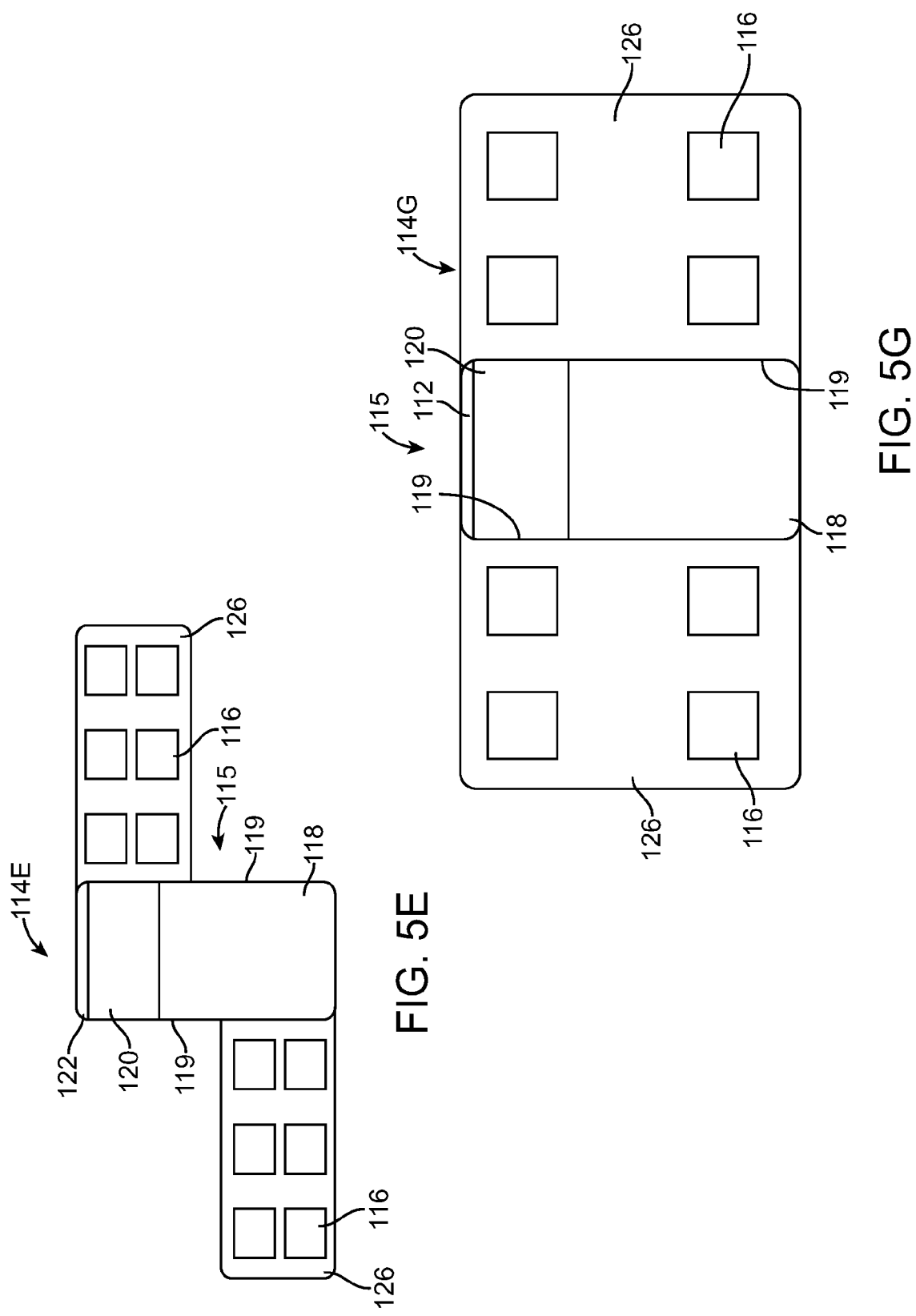

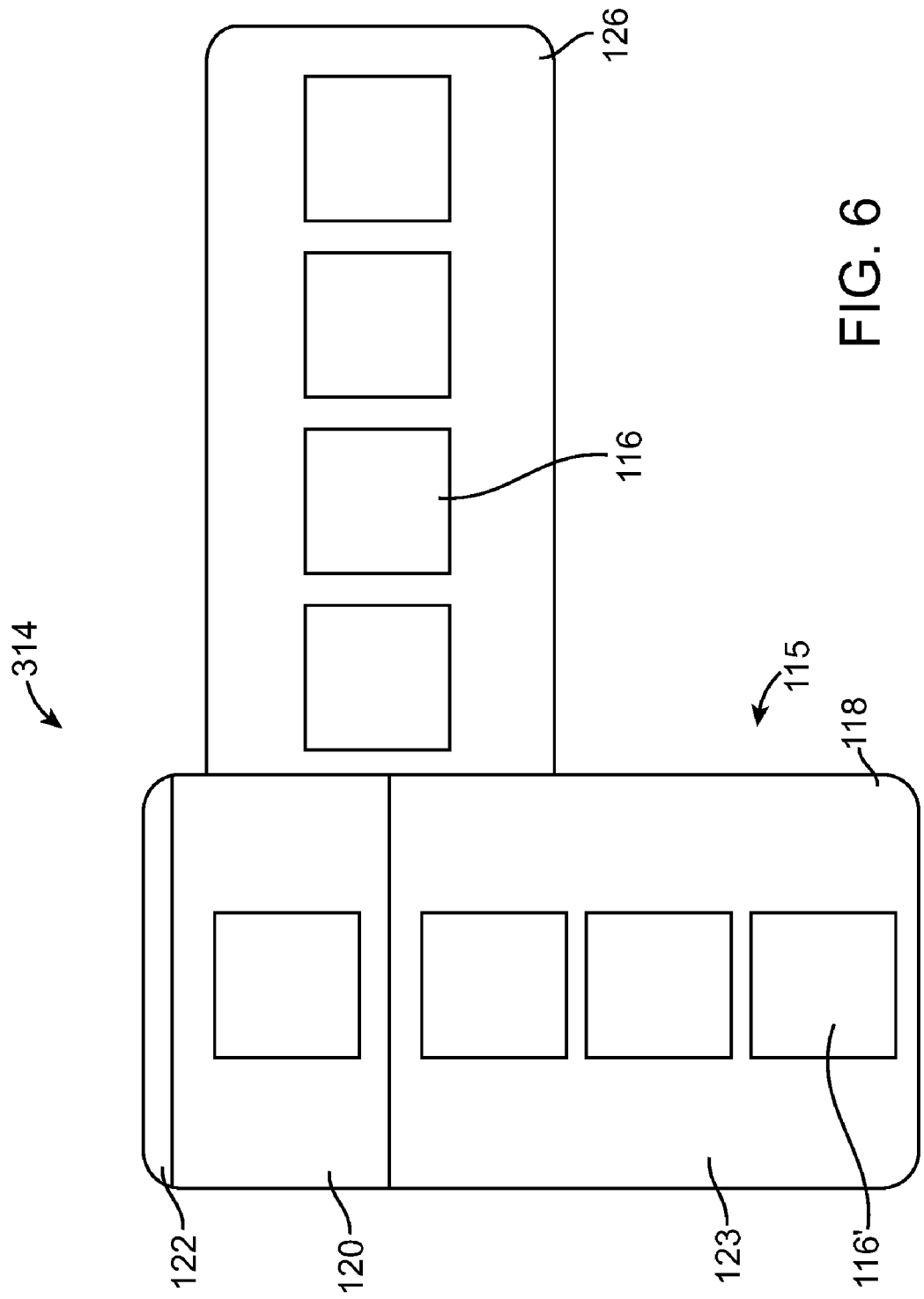

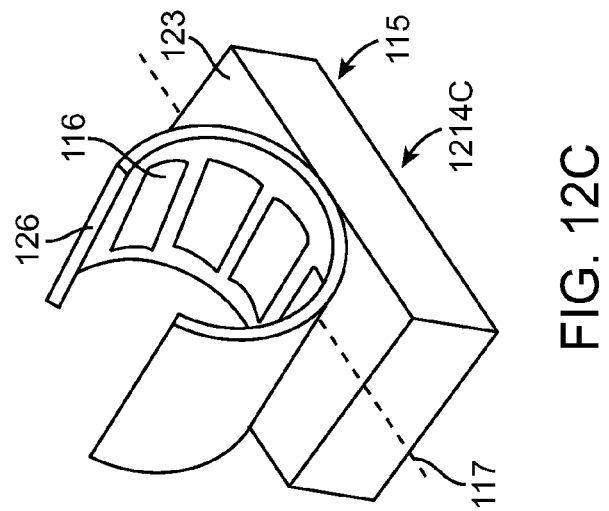
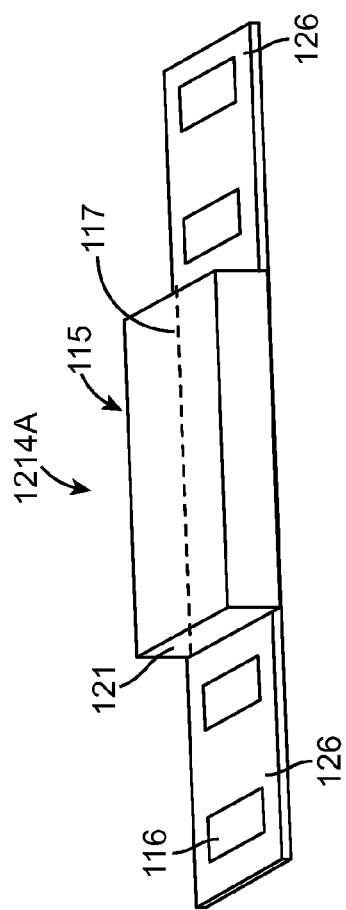
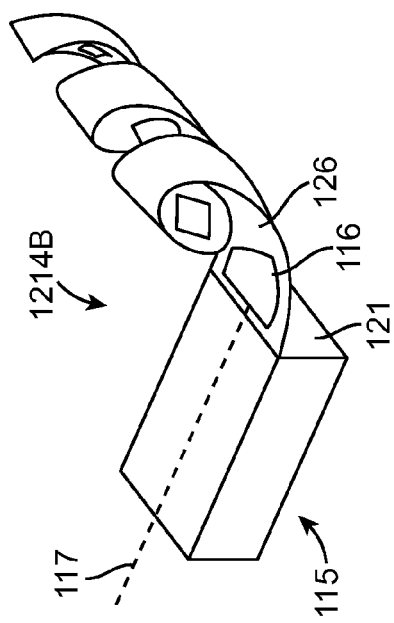
FIG. 12A
FIG. 12B
FIG. 12C

MICROSTIMULATOR WITH FLAP ELECTRODES

FIELD OF THE INVENTION

The present invention relates to tissue stimulation systems, and more particularly, to an implantable microstimulator that can still operate effectively after migration occurs.

BACKGROUND OF THE INVENTION

Implantable neurostimulation systems have proven therapeutic in a wide variety of diseases and disorders. Pacemakers and Implantable Cardiac Defibrillators (ICDs) have proven highly effective in the treatment of a number of cardiac conditions (e.g., arrhythmias). Spinal Cord Stimulation (SCS) systems have long been accepted as a therapeutic modality for the treatment of chronic pain syndromes, and the application of tissue stimulation has begun to expand to additional applications such as angina pectoralis and incontinence. Deep Brain Stimulation (DBS) has also been applied therapeutically for well over a decade for the treatment of refractory chronic pain syndromes, and DBS has also recently been applied in additional areas such as movement disorders and epilepsy. Further, in recent investigations, Peripheral Nerve Stimulation (PNS) systems have demonstrated efficacy in the treatment of chronic pain syndromes and incontinence, and a number of additional applications are currently under investigation. Furthermore, Functional Electrical Stimulation (FES) systems, such as the Freehand system by NeuroControl (Cleveland, Ohio), have been applied to restore some functionality to paralyzed extremities in spinal cord injury patients.

Thus, a wide variety of medical conditions and disorders have been successfully treated using implanted stimulators. Such stimulators will typically stimulate internal tissue, such as a nerve, muscle, organ, or the like, by emitting an electrical stimulation current according to programmed stimulation parameters.

One class of such implantable stimulators are typically characterized by a small, cylindrical or rounded-corner rectangular housing that contains electronic circuitry that produces the desired electric stimulation current between spaced electrodes that are disposed on the external surface of the stimulator housing. These stimulators, also referred to as microstimulators, are implanted proximate to the target tissue so that the stimulation current produced by the electrodes stimulates the target tissue to reduce symptoms or otherwise provide therapy for a wide variety of conditions and disorders.

In one embodiment, illustrated in FIGS. 1A and 1B, a microstimulator 14 has a housing 15 that generally includes a battery 18, a tube assembly 20 that houses the active electronic circuitry, and a feed-through assembly 22. Electrodes 16 are affixed to the external surface of the housing 15. A more detailed description of the components of the microstimulator 14 may be found in U.S. Patent Application Publication No. 2007/0112404, which is hereby expressly incorporated by reference. Since the electrodes 16 are disposed on the external surface of the microstimulator 14, it is necessary to position the microstimulator 14 directly over a target tissue site, e.g., a target nerve 12. Further, due to structural anatomical limitations (e.g., in the ankle for tibial nerve stimulation), it is often necessary to position the microstimulator 14 parallel (as shown in FIG. 1A), rather than perpendicular, to the target site 12. Significantly, proper location and maintenance of the microstimulator position are crucial in order to continuously achieve efficacious therapy. If the position of the microstimulator 14 shifts away from the target stimulation site 12 due to migration for example, as depicted in FIG. 1B, it is possible that the patient will receive little benefit from the implanted microstimulator 14. Thus, the effectiveness of the implanted microstimulator 14 may be significantly decreased due to migration. It is therefore important that the microstimulator 14 be accurately located at the target site 12 and that the microstimulator 14 be securely maintained at the target site 12.

However, it is difficult to avoid migration of the implanted microstimulator. There thus remains a need for a microstimulator that can be positioned adjacent to a target stimulation site, yet can still operate effectively if migration occurs.

SUMMARY OF THE INVENTION

In accordance with a first aspect of the present inventions, an implantable stimulator is provided. The implantable stimulator includes a casing that has an interior cavity. Stimulation circuitry is housed in the interior cavity of the casing. The implantable stimulator further comprises a flap coupled directly to the casing. The flap may include two lateral end edges, two longitudinal side edges, and two planar surfaces. One of the edges of the flap may be coupled directly to the casing. For example, one of the lateral end edges of the flap may be coupled directly to the casing. The flap may have a pre-shaped, curved configuration.

The implantable stimulator also includes one or more electrodes disposed on the flap. The casing may be an elongate casing having a longitudinal axis and the one or more electrodes may extend laterally relative to the longitudinal axis of the casing. The one or more electrodes may include a plurality of cathodes adjacent to a single elongated anode or a plurality of cathodes positioned between two elongated anodes.

The implantable stimulator may also include another flap directly coupled to the casing and another one or more electrodes disposed on the other flap. In this embodiment, the flaps may be symmetrically or asymmetrically coupled to opposite sides of the casing.

In accordance with a second aspect of the present inventions, a method for performing a medical procedure on a patient using a microstimulator having a stimulation circuitry casing, a flap coupled directly to the casing, and electrodes disposed on the flap is provided. The method includes implanting the microstimulator in the patient, such that the electrodes extend laterally over a target nerve. Implanting the microstimulator may include positioning the casing substantially parallel to the target nerve. The method for performing the medical procedure on the patient also includes operating the microstimulator to apply stimulation to the target nerve.

In accordance with a third aspect of the present inventions, an implantable stimulator is provided. The implantable stimulator includes a casing that has an interior cavity and stimulation circuitry housed in the interior cavity of the casing. The implantable stimulator also includes one or more electrodes coupled to the stimulation circuitry for generating an electric field and a flap coupled directly to the casing, wherein the flap is configured for shaping the electric field generated by the electrodes. The one or more electrodes may be disposed on a surface of the casing.

In accordance with a fourth aspect of the present inventions, an implantable stimulator is provided. The stimulator includes a casing having an interior cavity and stimulation circuitry housed in the interior cavity of the casing. The stimulator also includes an electrically insulative coating disposed on the casing and an electrically insulative flap coupled to the casing, wherein the coating and the flap are contiguous. The coating and the flap may be composed of the same material. The flap may have a pre-shaped curved configuration. One or more electrodes are disposed on the flap.

In an optional embodiment, the stimulator may further comprise another flap coupled to the casing, wherein the coating and the other flap are contiguous. Another one or more electrodes may be disposed on the other flap.

Other and further aspects and features of the invention will be evident from reading the following detailed description of the preferred embodiments, which are intended to illustrate, not limit, the invention.

BRIEF DESCRIPTION OF THE DRAWINGS

The drawings illustrate the design and utility of preferred embodiments of the present invention, in which similar elements are referred to by common reference numerals. In order to better appreciate how the above-recited and other advantages and objects of the present inventions are obtained, a more particular description of the present inventions briefly described above will be rendered by reference to specific embodiments thereof, which are illustrated in the accompanying drawings. Understanding that these drawings depict only typical embodiments of the invention and are not therefore to be considered limiting of its scope, the invention will be described and explained with additional specificity and detail through the use of the accompanying drawings in which:

FIGS. 3A' and 3A" are plan views of microstimulators constructed in accordance with embodiments of the present inventions that are respectively implanted non-orthogonal and perpendicular to a target nerve;

FIGS. 5A-7B are plan views of other exemplary implantable microstimulators constructed in accordance with embodiments of the present inventions;

FIGS. 12A-12C are perspective views of other exemplary implantable microstimulators constructed in accordance with embodiments of the present inventions;

DETAILED DESCRIPTION OF THE EMBODIMENTS

Figure 2:
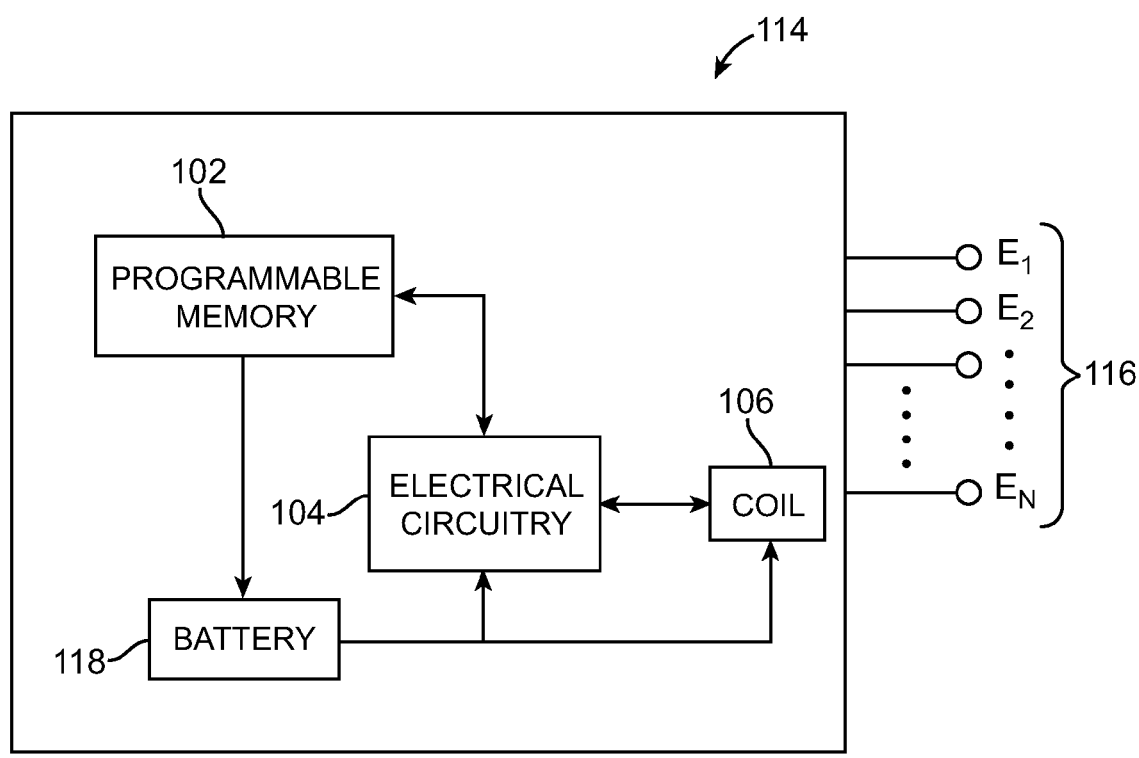
FIG. 2 is a block diagram illustrating a number of components of an implantable microstimulator constructed in accordance with an embodiment of the present inventions.

Turning to FIG. 2, an exemplary microstimulator 114 constructed in accordance with one embodiment of the present inventions will be described. Such a microstimulator 114 is small enough to be implanted almost anywhere in the human body for treatment of a wide variety of diseases and disorders, as discussed previously herein. The microstimulator 114 generally includes electrodes 116, an energy storage device (and in particular, a battery 118), a programmable memory 102, active electrical circuitry 104, and a coil 106.

The battery 118 is configured to output a voltage used to supply the various components within the stimulator 114 with power. The battery 118 also provides power for any stimulation current applied by the stimulator 114 to the stimulation site. The battery 118 may be a primary battery, a rechargeable battery, a capacitor, or any other suitable power source.

The coil 106 is configured to receive and/or emit electromagnetic energy (also referred to as a radio frequency (RF) field) that is used to communicate with or receive power from one or more external devices that support the implanted stimulator 114, such as a patient handheld programmer, a clinician programming station, and/or an external charger (all not shown), the details of which will not be described herein for purposes of brevity, but may, for example, be found in U.S. Patent Application Publication No. 2007/0112404, previously incorporated by reference elsewhere herein. Such communication and/or power transfer may include, but is not limited to, transcutaneously receiving data from the external device, transmitting data to the external device, and/or receiving power used to recharge the battery 118.

The programmable memory unit 102 is used for storing one or more sets of data, for example, electrical stimulation parameters. The programmable memory 102 allows a patient, clinician, or other user of the stimulator 114 to adjust the electrical stimulation parameters to levels that are safe and efficacious for a particular medical condition and/or for a particular patient. The electrical stimulation parameters may control various parameters of the stimulation current applied to the stimulation site including, but not limited to, the frequency, pulse width, amplitude, burst pattern (e.g., burst on time and burst off time), duty cycle or burst repeat interval, ramp on time and ramp off time of the stimulation current that is applied to the stimulation site. The programmable memory 102 may be any type of memory unit such as, but not limited to, random access memory (RAM), static RAM (SRAM), a hard drive, or the like.

The electrodes 116 (labeled $E_1$-$E_N$) are configured to apply the electrical stimulation current to the stimulation site. As depicted in FIG. 2, there may be any number of electrodes 116 as best serves a particular application. In some examples, one or more of the electrodes 116 may be designated as stimulating electrodes and one of the electrodes 116 may be designated as an indifferent electrode used to complete one or more stimulation circuits. Any of the electrodes 116 may be anodes or cathodes and the polarity of each electrode 116 may be reprogrammed.

The active electrical circuitry 104 is configured to produce electrical stimulation pulses that are delivered to the stimulation site via the electrodes 116. The electrical circuitry 104 may be configured to produce mono-polar or multi-polar stimulation. The electrical circuitry 104 may include one or more processors configured to decode stimulation parameters and generate the corresponding stimulation pulses. In some embodiments, the stimulator 114 has at least four channels and drives up to sixteen electrodes or more. The active electrical circuitry 104 may include additional circuitry such as capacitors, integrated circuits, resistors, coils, and the like configured to perform a variety of functions as best serves a particular application.

Figure 1B:
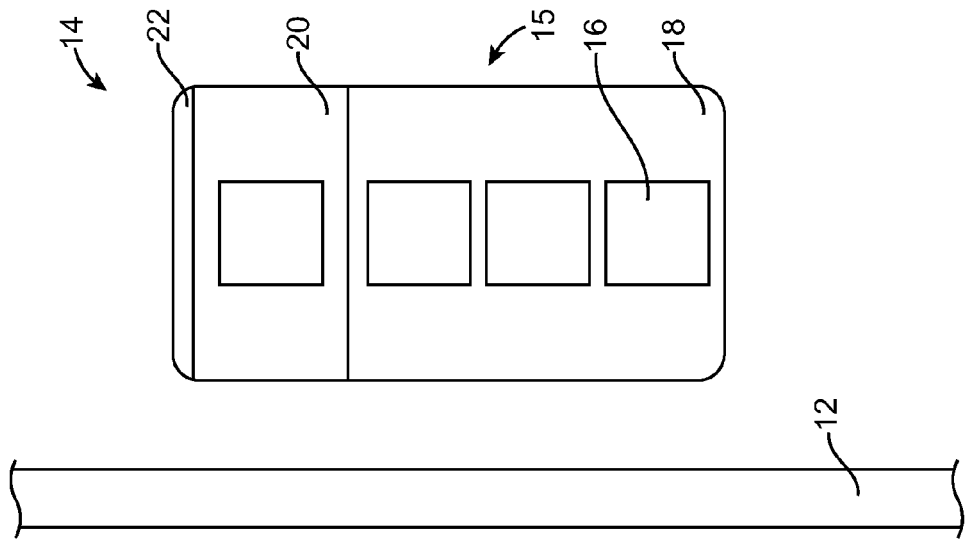
FIGS. 1A and 1B are plan views of a microstimulator before migration and after migration, respectively.
Figure 1A:
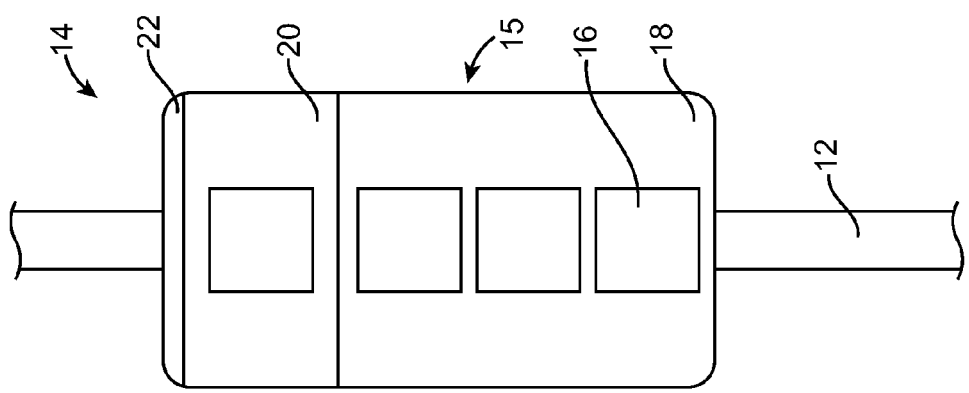

As described previously herein, the electrodes 116 may be attached to the external surface of the housing of the implantable microstimulator 114. Such an arrangement, however, requires accurate positioning of the microstimulator 114 directly over a target stimulation site, and, as shown in FIGS. 1A and 1B, migration of the microstimulator may reduce the effectiveness of the device. Therefore, embodiments of the present invention relate to implantable microstimulators that can still operate effectively after migration occurs. In this manner, embodiments may advantageously include a microstimulator with electrodes that extend laterally (i.e., at an angle of between 30 and 150 degrees) relative to a longitudinal axis of the microstimulator casing. Thus, the microstimulator may be implanted adjacent to a target nerve, and, due to the arrangement of the electrodes, may still operate effectively even if the microstimulator 114 migrates away from the nerve.

Figure 3A:
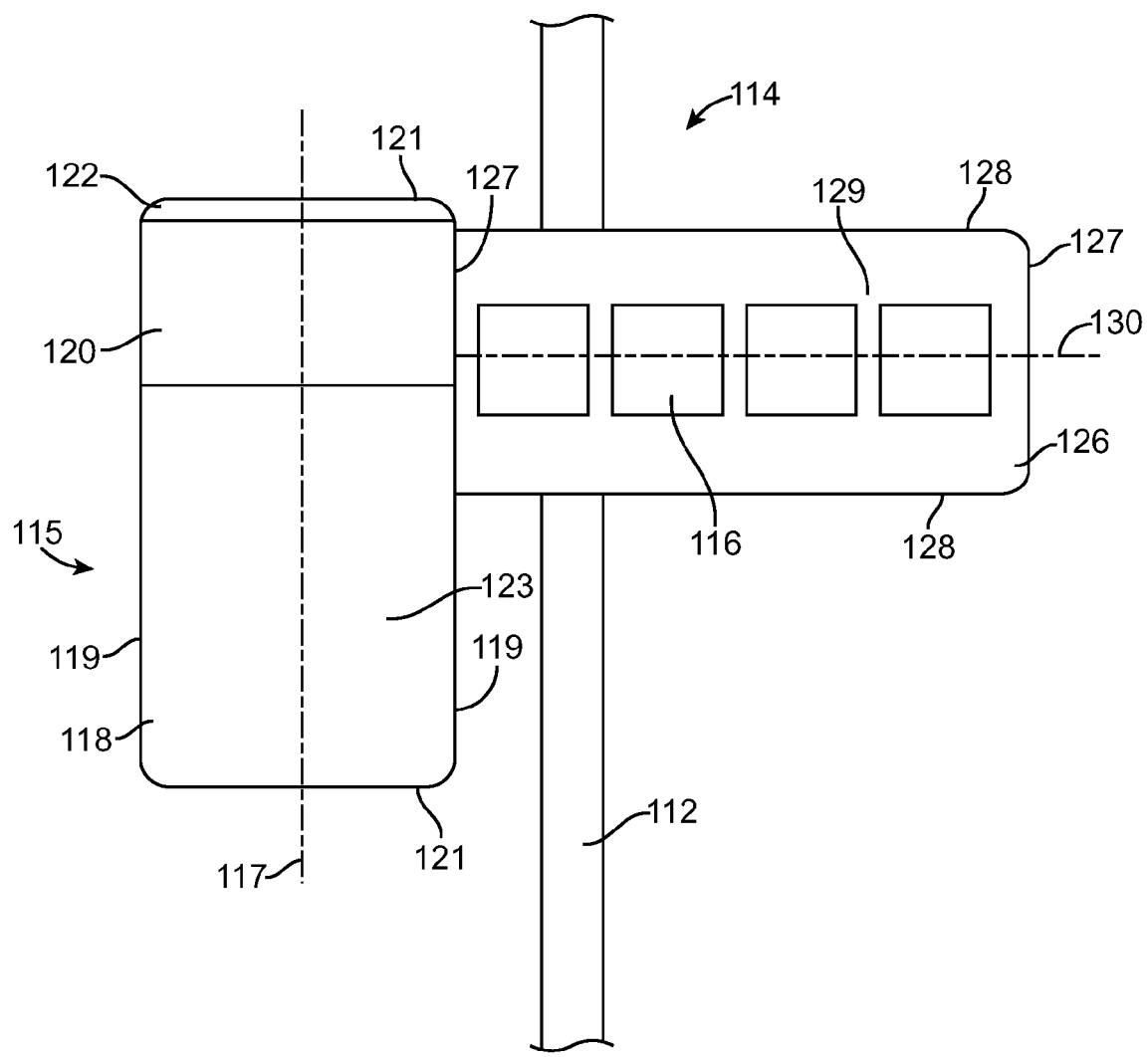
FIGS. 3A and 3B are plan views of a microstimulator constructed in accordance with an embodiment of the present inventions before migration and after migration, respectively.
Figure 3B:
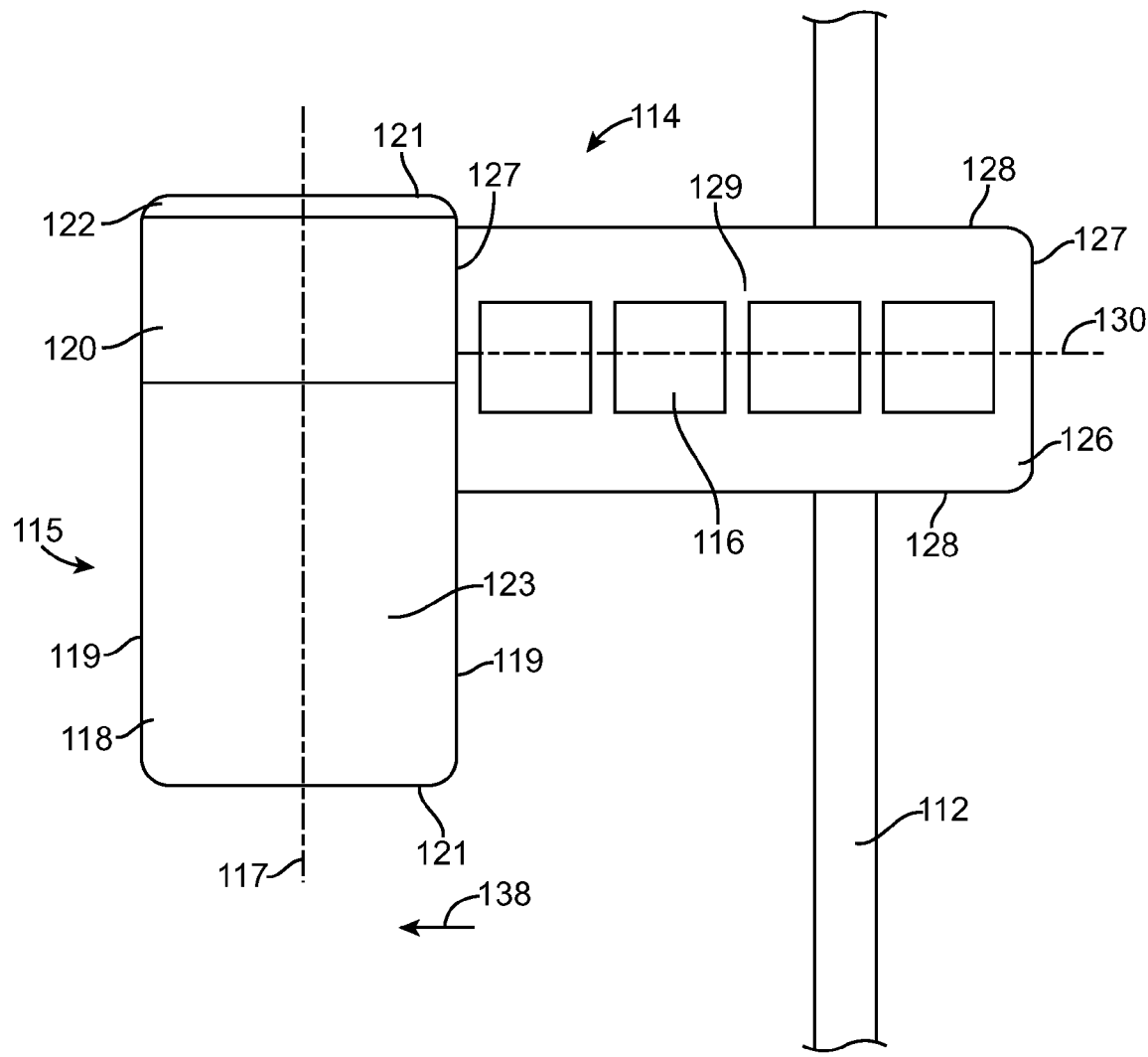

Turning now to FIGS. 3A and 3B, one example of a microstimulator 114 constructed in accordance with one embodiment of the present invention will be described. The microstimulator 114 includes an elongate microstimulator casing 115 and an electrode flap 126 perpendicularly coupled directly to the casing 115. The casing 115 includes a tube assembly 120 that is coupled on one end to the battery 118 and on the other end to a feed-through assembly 122. The tube assembly 120 includes an interior cavity that houses the active electrical circuitry 104, the programmable memory 102, and the coil 106 (all of which are depicted diagrammatically in FIG. 2). As described in further detail below, the active electrical circuitry 104 within the tube assembly 120 is coupled to electrodes 116 on the flap 126 via a number of feed-throughs (not shown) in the feed-through assembly 122. Any other components of the microstimulator 114 that may best serve a particular application may also be housed within the tube assembly 120. The microstimulator casing 115 may also include an indifferent electrode (not shown).

Notably, the microstimulator 114 is designed to stimulate tissue that is local to its implantation site in that it does not include a lead on which the electrodes 116 are mounted. Rather, the electrode flap 126 is attached directly to the casing 115 without any intervening components. Thus, an additional component in the form of a lead need not be implanted within the patient. The entire stimulation means is advantageously implanted at the site where stimulation is needed.

The casing 115 is generally rectangular, although it should be understood that the casing 115 may alternatively be cylindrical, elongated oval, square, or any other shape that may house a battery and electrical circuitry. The casing 115 has a longitudinal axis 117, two longitudinal side surfaces 119 that are parallel to the longitudinal axis 117, two lateral end surfaces 121 that are perpendicular to the longitudinal axis 117, and two planar surfaces 123 (only the upper planar surface 123 can be seen in FIGS. 3A and 3B) that are parallel to the longitudinal axis 117. In the exemplary embodiment, the longitudinal side surfaces 119 are about 26-30 mm long, the lateral end surfaces 121 are about 6.5-8 mm wide, and the thickness (not shown) of the casing 115 is about 3.5-5 mm.

The electrode flap 126 has a longitudinal axis 130, two longitudinal side edges 128 that are parallel to the longitudinal axis 130, two lateral end edges 127 that are perpendicular to the longitudinal axis 130, and two planar surfaces 129 (only the upper planar surface 129 can be seen in FIGS. 3A and 3B) that are parallel to the longitudinal axis 130. The electrodes 116 are attached to the upper planar surface 129 of the flap 126. One of the lateral end edges 127 of the electrode flap 126 is attached directly to one of the longitudinal side surfaces 119 of the casing 115. In this manner, the electrodes 116 extend substantially perpendicular relative to the longitudinal axis 117 of the casing 115 in order to account for possible lateral migration of the microstimulator 114.

In other embodiments, the electrodes 116 may extend laterally at other angles that are non-orthogonal to the longitudinal axis 117 of the casing 115. For example, as shown in FIG. 3A', a microstimulator 114' includes electrodes 116 on the electrode flap 126 that extend laterally relative to the longitudinal axis 117 of the casing 115 at an angle 113 of about 45 degrees. It should be understood that the angle 113 between the electrodes 116 on the flap 126 and the casing 115 may alternatively be an obtuse angle and that the electrodes 116 and the flap 126 may extend laterally at any angle, e.g. between 30 and 150 degrees, relative to the longitudinal axis 117 of the casing 115.

Since there is not a lead between the electrodes 116 and the casing 115, the entire microstimulator 114, including the casing 115 and the electrode flap 126, is implantable adjacent to a target stimulation site (and in particular, a target nerve 112). The casing 115 may be implanted parallel to the target nerve 112, but is not necessarily implanted directly over the target nerve 112. Significantly, because the casing 115 and electrode flap 126 are designed to act as a single body to facilitate the implantation process, migration of the casing 115 causes simultaneous migration of the electrode flap 126 and vice versa. However, since the flap 126 extends laterally, lateral migration of the microstimulator 114 does not reduce the effectiveness of the microstimulator 114. For example, as shown in FIG. 3B, even if the microstimulator casing 115 migrates in the direction indicated by arrow 138, the electrodes 116 may still be positioned over the target nerve 112 and the microstimulator 114 can still be operated effectively. Similarly, the microstimulator 114' depicted in FIG. 3A' may remain effective even after migration occurs. The microstimulators 114 and 114' may require re-programming after migration, but do not require surgery and re-positioning of the microstimulators 114 and 114' after migration.

It should be understood that, although the microstimulator 114 is described as being particularly useful for being implanted with the casing 115 parallel to the target nerve 112 and for remaining effective after migration, the microstimulator 114 may be useful, under some circumstances, when the casing 115 is perpendicular to the target nerve 112, as depicted in FIG. 3A", or is at another angle that is non-orthogonal to the target nerve 112. For example, the microstimulator 114' shown in FIG. 3A' is depicted as being implanted with the longitudinal axis 117 of the casing 115 at an angle of about 30 degrees relative to the target nerve 112, but may alternatively be implanted at any other angle (e.g., between 30 and 150 degrees) relative to the target nerve 112.

The electrode flap 126 may be formed of any suitable biocompatible material that may be, for example, soft and flexible (i.e., silicone, polyurethane, PEEK, polyimide, etc.), hard and rigid (i.e., metal, ceramics, etc.), semi-rigid, semi-flexible, and so forth. Further, the electrode flap 126 may be attached to the casing 115 using medical adhesive or any other suitable attachment material or device.

Figure 4A:
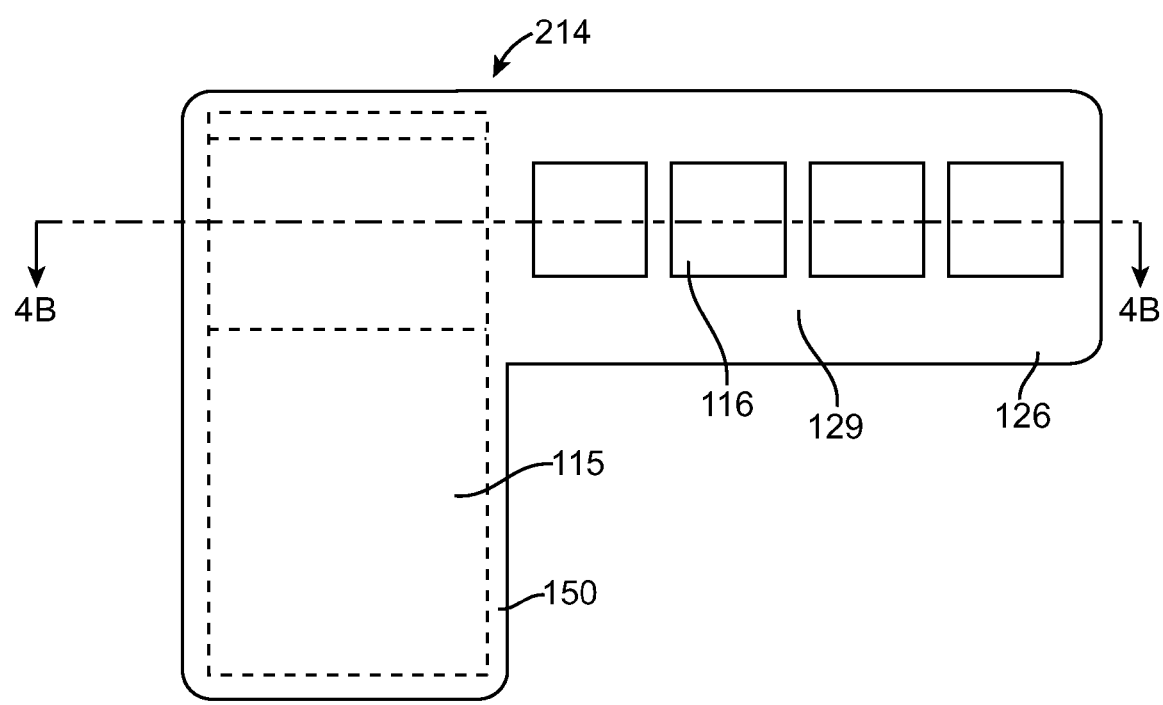
FIG. 4A is a plan view of another exemplary implantable microstimulator constructed in accordance with embodiments of the present inventions.
Figure 4B:
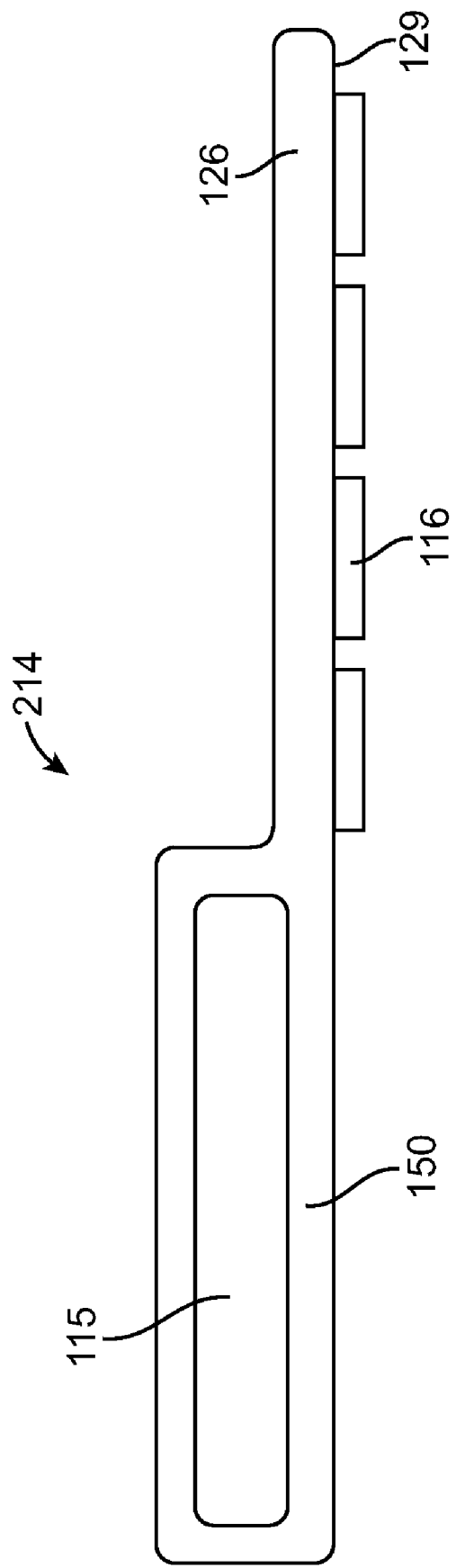
FIG. 4B is a cross-sectional view of the implantable microstimulator shown in FIG. 4A, taken along line 4B-4B in FIG. 4A.

Alternatively, the microstimulator includes an insulative coating and an electrode flap formed simultaneously and contiguously with the insulative coating. For example, with reference to FIGS. 4A and 4B, a microstimulator 214 includes an electrically insulative coating 150 covering the casing 115 (shown in phantom in FIG. 4A). The electrode flap 126 is contiguous with the coating 150. In other words, the coating 150 and the flap 126 are a single, integral piece and the flap 126 is composed of the same material as the coating 150. Prior to applying the coating 150 and the flap 126, the electrodes 116 are coupled to the feedthrough assembly of the casing 115 using, for example, wires or another such coupling mechanism (not shown). The single integral piece forming the coating 150 and the flap 126 may be pre-made and then attached to the casing 115 or may be applied directly to the casing 115. For example, the coating 150 and the flap 126 may be formed by injection molding, compression molding, lamination, or the like.

Figure 5A:
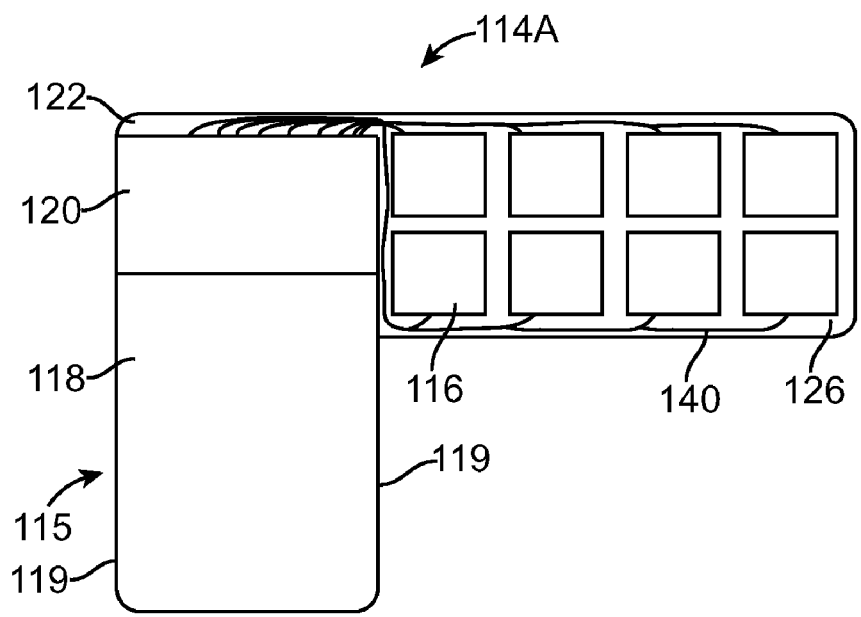

As mentioned previously herein, the active electrical circuitry 104 within the tube assembly 120 is coupled to the electrodes 116. One exemplary mechanism for coupling the circuitry 104 to the electrodes 116 is described with reference to FIG. 5A. A microstimulator 114A includes a plurality of wires 140 for coupling the respective plurality of electrodes 116 to the active circuitry 104 (see FIG. 2) within the tubular assembly 120. The plurality of wires 140 pass through a respective plurality of feed-throughs (not shown) in the feedthrough assembly 122. Alternatively, the feed-throughs could be located elsewhere on the casing 115. For example, one or more of the feed-throughs may be located on one of the longitudinal sides 119 of the casing 115. In another alternative, the casing 115 may have only one feed-through and a ribbon cable that includes a plurality of wires, each of which is coupled to one of the respective plurality of electrodes 116 on the flap 126. In still another alternative, the electrodes 116 may be coupled to the circuitry 104 using a printed circuit board or other electrical connection mechanisms. Notably, the electrical connection between the electrodes 116 and the circuitry 104 does not include a lead.

In previous embodiments, the electrode flap is coupled to the microstimulator casing by coupling one of the lateral edges of the flap to an upper portion of one of the longitudinal sides of the casing. However, it should be well understood that any of the planar surfaces or edges of the electrode flap may be attached to any of the planar surfaces or sides of the microstimulator casing in a manner that maximizes the potential that the electrodes will be located adjacent to a target stimulation site after migration of the microstimulator.

Figure 5B:
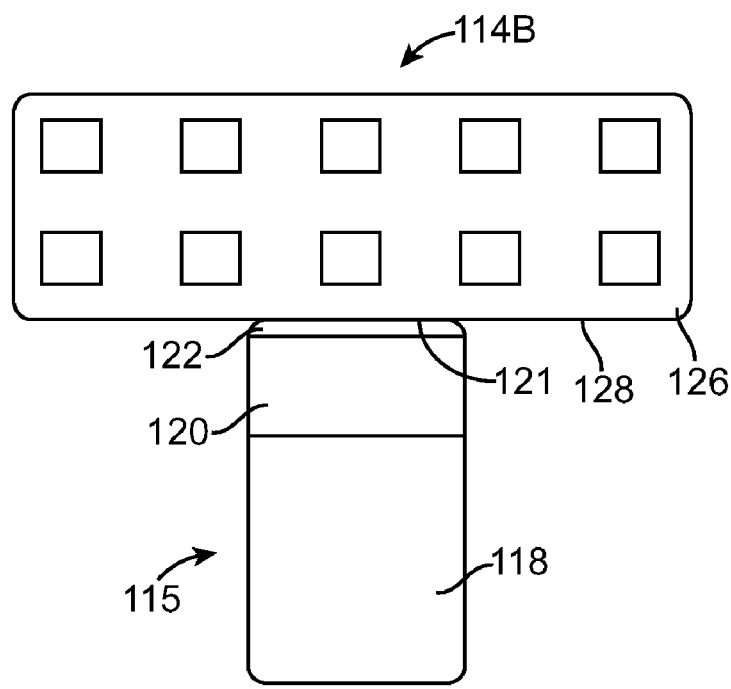

For example, with reference to FIG. 5B, a microstimulator 114B includes an electrode flap 126 that is coupled to one of the lateral end surfaces 121 of the casing 115. In particular, one of the longitudinal side edges 128 of the electrode flap 126 is attached to one of the lateral end surfaces 121 of the casing 115 in roughly the middle of the longitudinal edge 128 of the flap 126, thereby forming a T-shaped configuration. However, it should be well understood that the lateral end surface 121 of the casing 115 may be attached anywhere along the length of the longitudinal edge 128 of the flap 126. For example, one of the end portions of the longitudinal edge 128 of the flap 126 may be attached to the lateral end surface 121 of the casing 115 to form an L-shaped configuration.

Figure 5C:
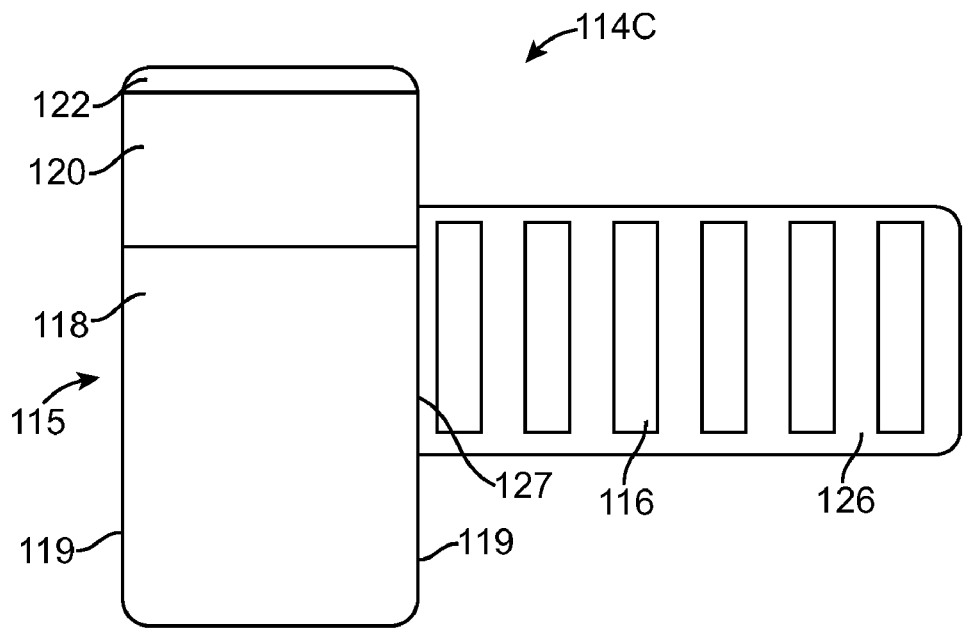

In another example, shown in FIG. 5C, a microstimulator 114C includes an electrode flap 126 that is coupled to one of the longitudinal side surfaces 119 of the casing 115, similar to the previous embodiments. However, in the example shown in FIG. 5C, the electrode flap 126 is positioned differently along the longitudinal side surface 119. In particular, one of the lateral end edges 127 of the electrode flap 126 is coupled to one of the longitudinal side surfaces 119 of the casing 115 at about the middle of the longitudinal side surface 119, thereby forming another T-shaped configuration.

Figure 5D:
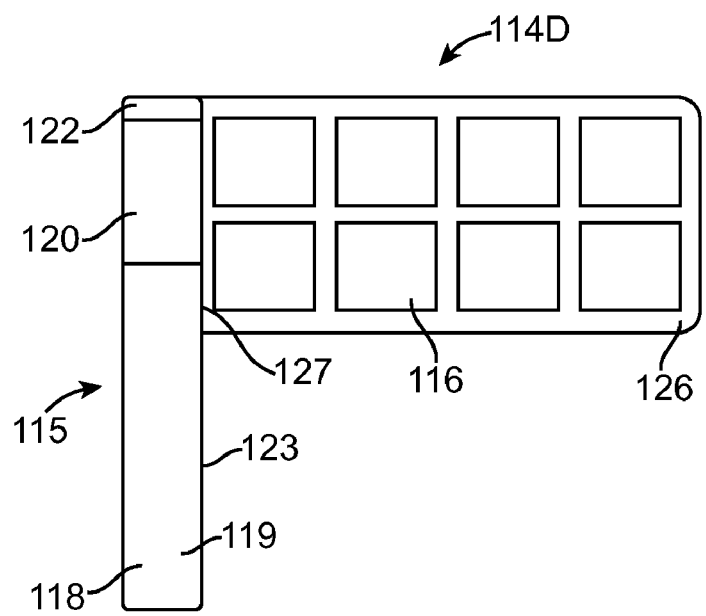

In still another example, shown in FIG. 5D, a microstimulator 114D includes an electrode flap 126 coupled to one of the planar surfaces 123 of the casing. In particular, one of the lateral edges 127 of the flap 126 is attached to an upper portion of one of the planar surfaces 123 of the casing 115.

Any of the previously described exemplary microstimulators may have additional electrode flaps coupled to the casing. For example, with reference to FIG. 5E, a microstimulator 114E includes two electrode flaps 126 that are attached to opposite longitudinal side surfaces 119 of the casing 115 in an asymmetrical manner. The flaps 126 are asymmetrically attached by attaching one of the flaps 126 (i.e., the flap 126 on the right in FIG. 5E) to an upper portion of one of the longitudinal side surfaces 119 of the casing 115 and attaching the other flap 126 (i.e., the flap 126 on the left in FIG. 5E) to a lower portion of the opposing longitudinal side surface 119. The flaps 126 may alternatively be attached to the casing in a symmetrical manner.

Figure 5F:
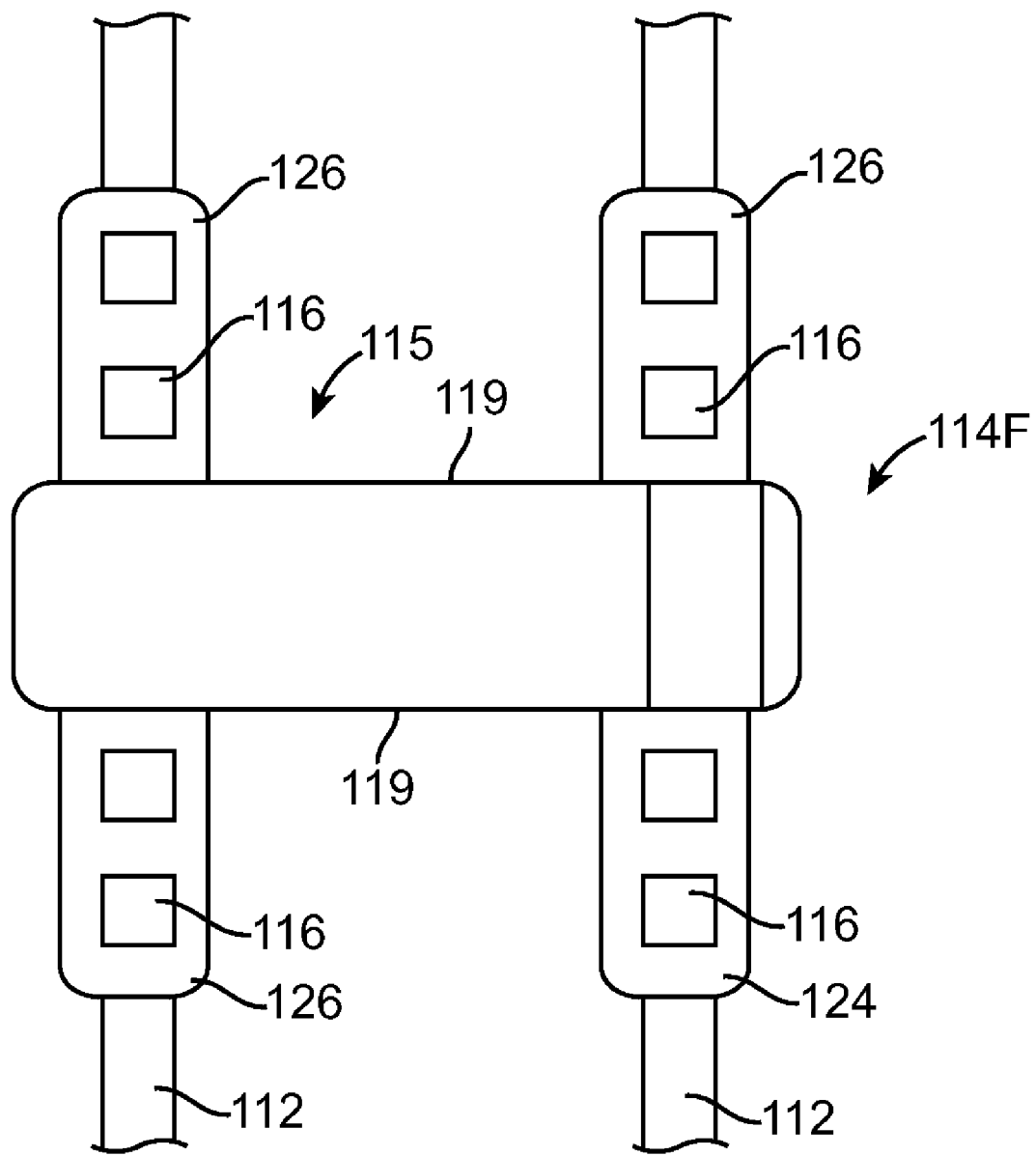

As another example, as shown in FIG. 5F, a microstimulator 114F may include four electrode flaps 126 that are attached to opposite longitudinal side surfaces 119 of the casing 115 in a symmetrical manner. Although the microstimulator 114F is depicted as being positioned with the casing 115 perpendicular to the target nerves 112 and the electrodes 116 extending parallel to the target nerves 112, as discussed above, the microstimulator 114F is particularly useful for being positioned with the casing 115 parallel to the target nerves 112 and the electrodes extending laterally relative to the target nerves 112.

Although the electrode flaps discussed above are depicted as being rectangular, a microstimulator may include one or more electrode flaps that are square, elliptical, or the like. For example, with reference to FIG. 5G, a microstimulator 114G includes two square-shaped electrode flaps 126 coupled to opposing longitudinal surfaces 119 of the casing 115. The lengths of the edges of the flaps 126 are substantially the same as the length of the casing 115, such that substantially the entire lengths of the longitudinal side surfaces 119 of the casing 115 are directly attached to the flaps 126.

The exemplary microstimulators described herein may have any number, shape, and arrangement of electrodes, depending on the particular application. For example, the microstimulators 114A, 114B and 114D in FIGS. 5A, 5B and 5D, respectively, include eight or ten electrodes arranged in two rows, the microstimulators 114C and 114F in FIGS. 5C and 5F, respectively, include a single row of two square or six rectangular electrodes on each flap, and the microstimulators 114E and 114G in FIGS. 5E and 5G, respectively, include two rows of two or three electrodes on each flap. Further, the electrodes 116 may be disposed on one or both planar surfaces 129 (i.e., the upper planar surface and the lower planar surface) of the flap 126.

Additional electrodes may be attached to one (or both) of the planar surfaces of the casing. For example, as shown in FIG. 6, a microstimulator 314 includes electrodes 116' on the upper planar surface 123 of the microstimulator casing 115 in addition to the electrodes 116 on the flap 126.

In the previous embodiments, the electrodes 116 on the flap 126 may be monopolar. That is, the electrodes 116 may be arranged to all have the same polarity, with the casing 115 being used as an electrode of opposite polarity, or the electrodes 116 may be configured such that there are an equal number of anodes and cathodes. However, as discussed briefly above, the electrodes 116 may have any desired polarity configuration and may be configured to have a multi-polar effect. In addition, the polarity of each electrode 116 may be reprogrammed.

Figure 7A:
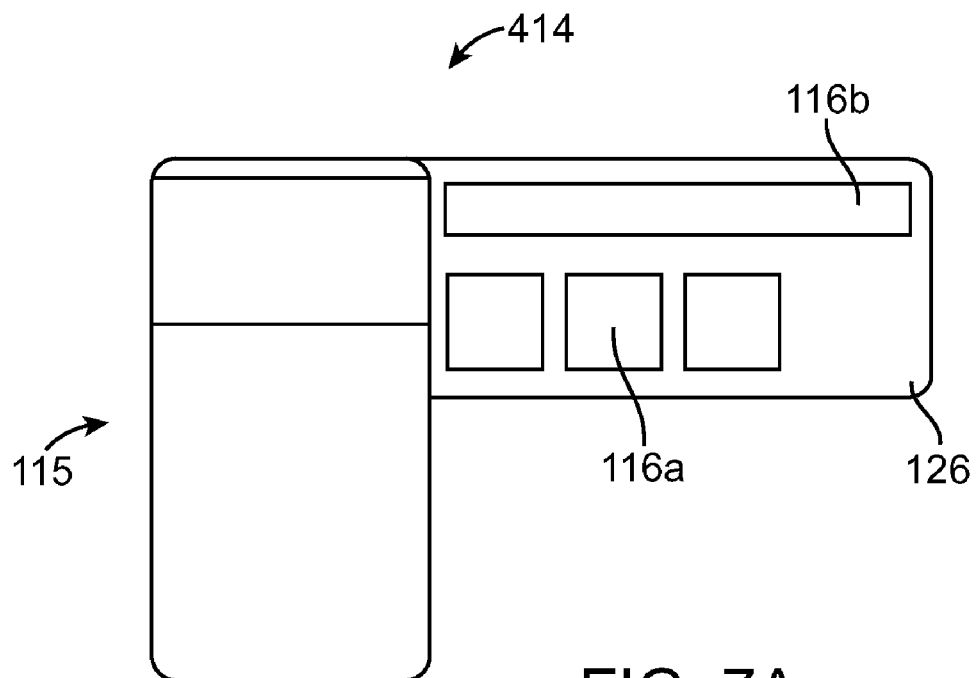

One example of a microstimulator 414 having a bipolar configuration is shown in FIG. 7A. The microstimulator 414 is similar to the previously described microstimulators, with the exception that the electrodes 116 on the flap 126 are arranged in a bipolar configuration. In particular, the microstimulator 414 includes a plurality of smaller electrodes 116*a* disposed along the length of the electrode flap 126 and an elongated electrode 116*b* having a length slightly less than the length of the electrode flap 126. The elongated electrode 116*b* has a polarity opposite to that of the smaller electrodes 116*a*. For example, the elongated electrode 116*b* may be configured as an anode and the smaller electrodes 116*a* may be configured as cathodes.

Figure 7B:
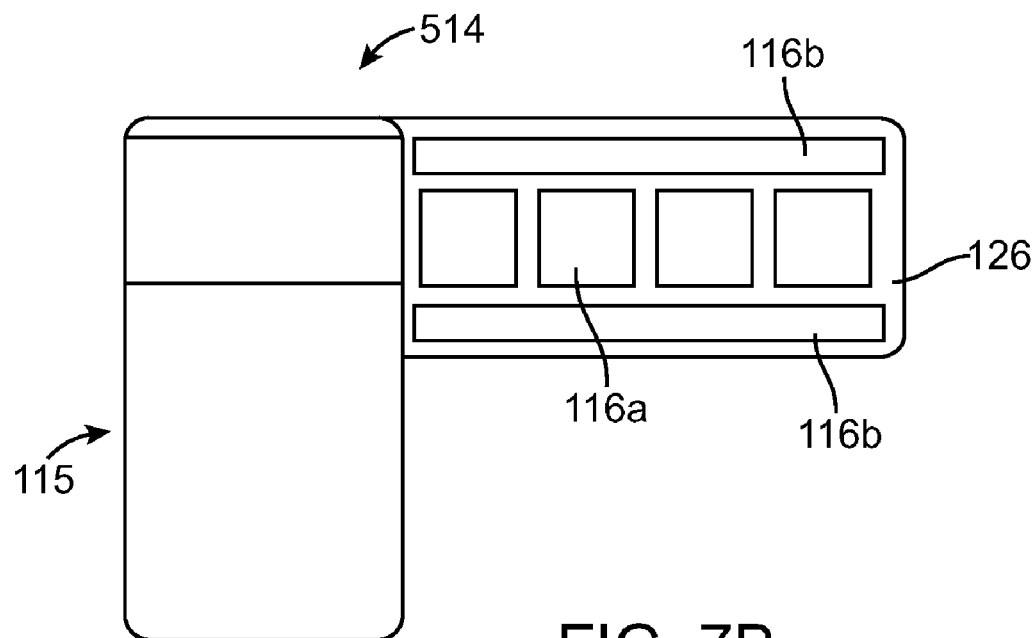

One example of a microstimulator 514 having a tripolar configuration is shown in FIG. 7B. The microstimulator 514 is similar to the previously described microstimulators, with the exception that the electrodes 116 on the flap 126 are arranged in a tripolar configuration. In particular, the microstimulator 514 includes a plurality of smaller electrodes 116*a* disposed along the length of the electrode flap 126, and two elongated electrodes 116*b* having a length slightly less than the length of the electrode flap 126. The smaller electrodes 116*a* are positioned between the elongated electrodes 116*b*. The polarity of the elongated electrodes 116*b* is opposite to that of the smaller electrodes 116*a*. For example, the elongated electrodes 116*b* may be configured as anodes and the smaller electrodes 116*a* may be configured as cathodes.

Although the electrode flaps have been described as having a flat shape, the electrode flaps may be curved in order to at least partially surround the targeted stimulation site. For example, with reference to FIG. 8A, a microstimulator 614 includes a single electrode flap 126 having a curved configuration that resembles a cuff. The flap 126 is curved such that the electrodes 116 face inwardly in order to face towards the target stimulation site. The curved configuration of the flap 126 may be pre-shaped.

Figure 8B:
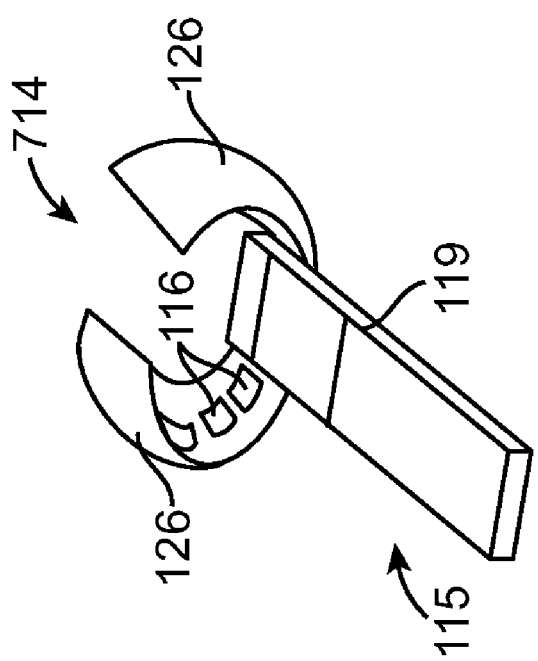
FIGS. 8A and 8B are perspective views of yet other exemplary implantable microstimulators constructed in accordance with embodiments of the present inventions.
Figure 8A:
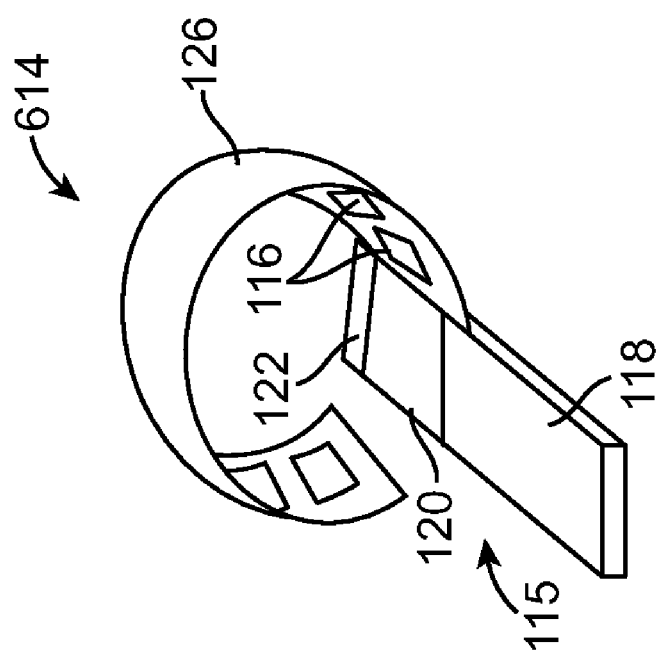

In a similar example, shown in FIG. 8B, a microstimulator 714 includes two curved electrode flaps 126 attached to opposite longitudinal side surfaces 119 of the microstimulator casing 115 in a symmetrical manner. Each of the curved flaps 126 forms a portion of the cuff configuration. The desired curved configuration may be pre-shaped.

Figure 9:
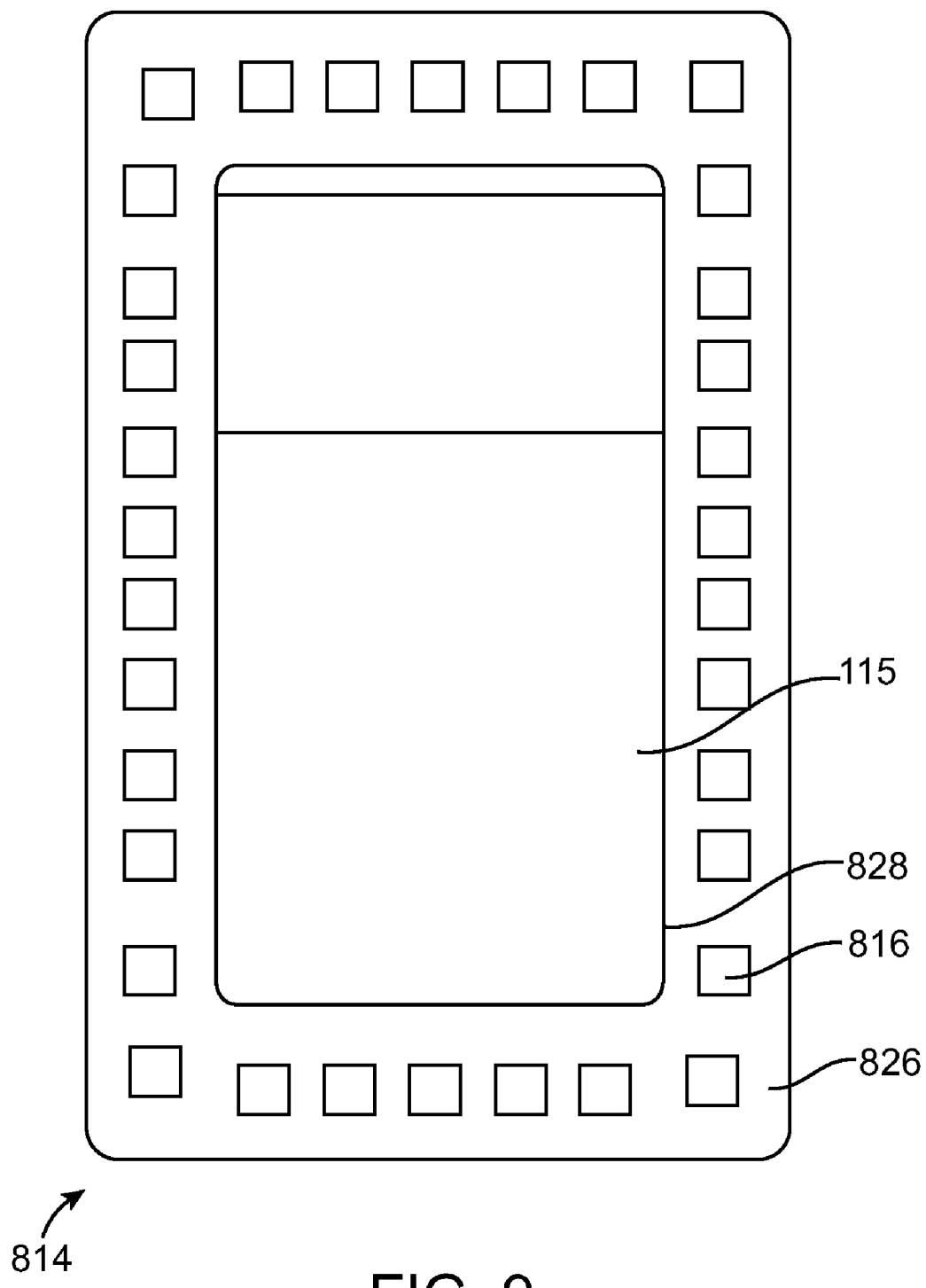
FIG. 9 is a plan view of still another exemplary implantable microstimulator constructed in accordance with embodiments of the present inventions.

Although the electrode flaps have been described as extending from one or two sides of the microstimulator casing, the electrode flap may extend radially from all sides of the casing. For example, with reference to FIG. 9, a microstimulator 814 includes an electrode flap 826 that extends perpendicularly and radially around the circumference of the microstimulator casing 115. The electrode flap 826 is generally ring shaped and the inner edge 828 of the ring is coupled directly to the sides of the microstimulator casing 115 such that the electrode flap 826 encircles the microstimulator casing 115. Although the microstimulator 814 is depicted with electrodes 816 positioned all the way around the ring-shaped electrode flap 826, it should be well understood that electrodes 816 may alternatively be positioned on selected portions of the electrode flap 826. In addition, although the microstimulator 814 is depicted with a rectangular casing 115 and a rectangular ring flap 826, it should be well understood that the casing 115 and flap 826 may have other shapes. For example, the casing 115 and the flap 826 may be square-shaped.

Figure 10A:
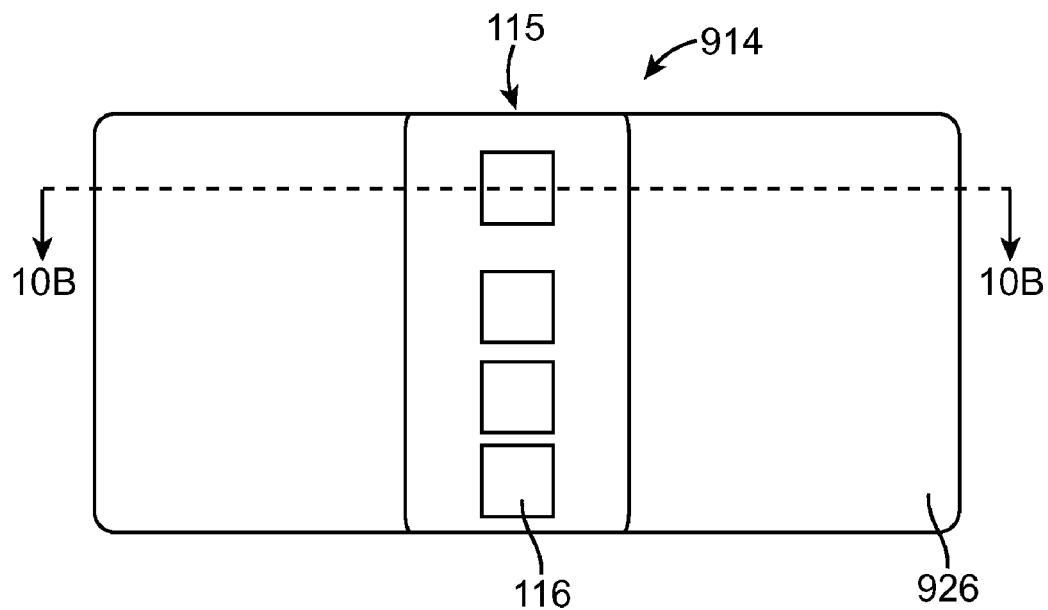
FIG. 10A is a plan view of yet another exemplary implantable microstimulator constructed in accordance with embodiments of the present inventions.
Figure 10B:
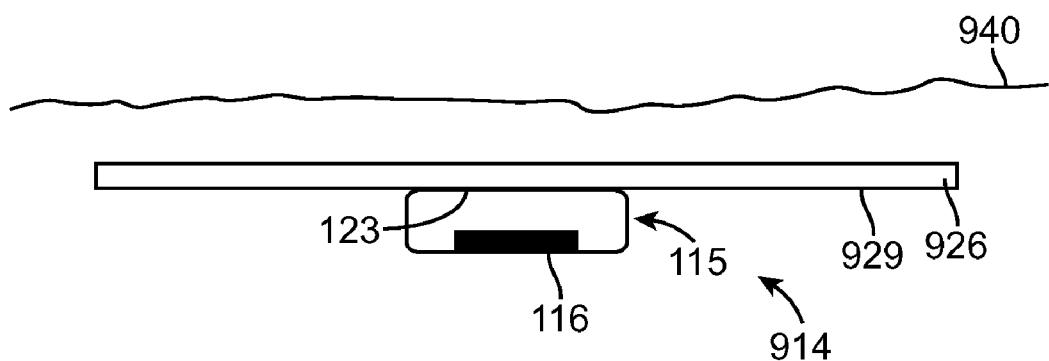
FIG. 10B is a cross-sectional view taken along line 10B-10B in FIG. 10A.

In the previous embodiments, the electrodes are positioned on the electrode flaps. However, the electrodes may be positioned on the microstimulator casing and the flap may be configured for directing, blocking, and/or shaping the electric field created by the electrodes of the microstimulator. For example, with reference to FIGS. 10A and 10B, a microstimulator 914 includes electrodes 116 coupled to the microstimulator casing 115 and a flap 926 that is perpendicularly coupled to the casing 115. In this example, the flap 926 has a length equal to that of the casing 115, and one of the planar surfaces 929 of the flap 926 is attached directly to one of the planar surfaces 123 of the casing 115. The microstimulator 914 is configured for being disposed under the skin surface 940 (see FIG. 10B) such that the flap 926 is positioned between the casing 115 and the skin surface 940. In this manner, the flap 926 is configured for directing stimulation to the target stimulation site and for blocking stimulation in the direction of the skin surface 940.

Although the use of the microstimulators above have been described as being used to advantageously compensate for lateral migration relative to a nerve, these microstimulators may be used for other applications as well. For example, as illustrated in FIGS. 11A-11D, some of these microstimulators may be used to stimulate cortical brain tissue. As shown in FIGS. 11A-11D, the microstimulator 114 is implanted by forming a cranial burr hole 1102, inserting the electrode flap 126 into the space 1104 between the brain 1106 and the inner surface of the skull bone 1108, and positioning the microstimulator casing 115 within the burr hole 1102 (as in FIGS. 11A and 11B) or within a recess 1110 or 1112 adjacent to the burr hole 1102 (as in FIGS. 11C and 11D). The flap 126 is oriented between the brain 1106 and the skull bone 1108, such that the electrodes 116 face the brain tissue 1106. In particular, the flap 126 may be placed between the dura (not shown) and the brain tissue 1106 or between the skull bone 1108 and the dura.

Figure 11A:
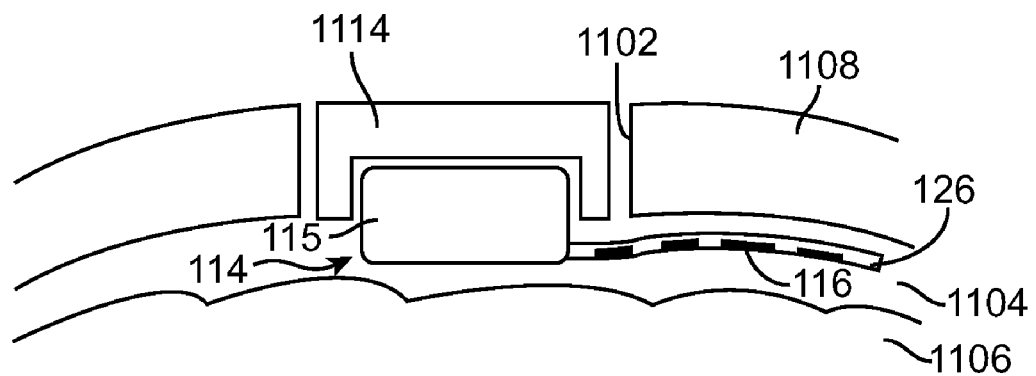
FIGS. 11A-11D are cross-sectional views of the exemplary implantable microstimulator depicted in FIGS. 3A and 3B being used in a cortical stimulation procedure.
Figure 11B:
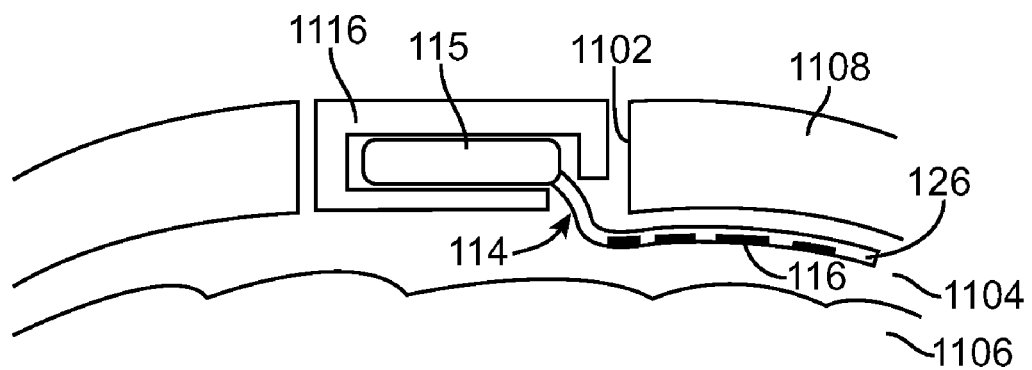
Figure 11C:
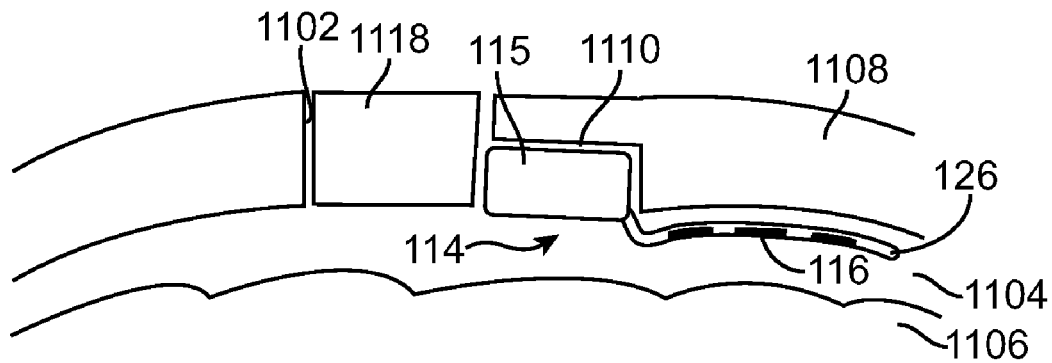
Figure 11D:
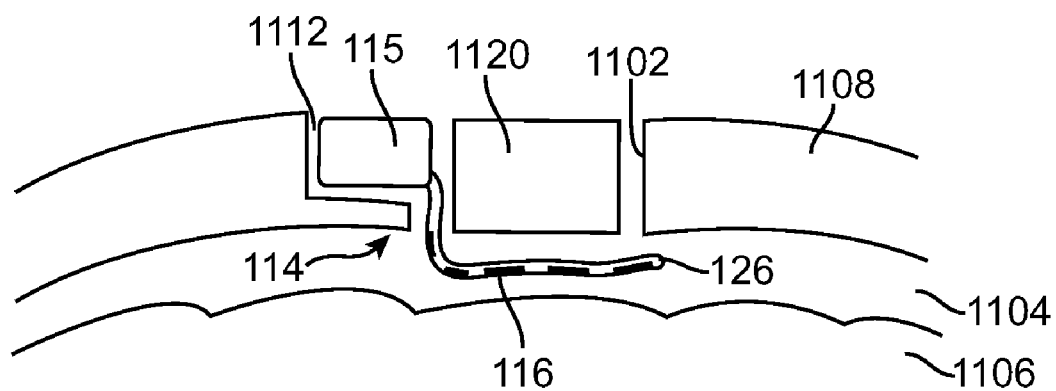

Burr hole plugs 1114 and 1116 depicted in FIGS. 11A and 11B, respectively, are designed for holding the microstimulator casing 115 in the desired position within the burr hole 1102. Alternatively, a conventional burr hole plug 1118 or 1120 is used, as shown in FIGS. 11C and 11D, respectively, but the implantation procedure requires the extra step of creating the recess 1110 or 1112 adjacent to the burr hole 1102. In a cortical stimulation procedure, after the microstimulator 114 is implanted in the manner shown in one of FIGS. 11A-11D, the microstimulator 114 is operated to apply stimulation to the brain tissue 1106.

Figure 12D:
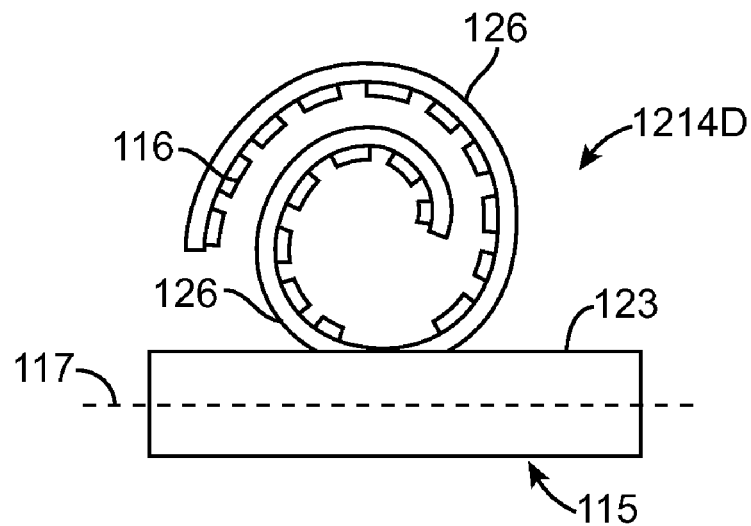
FIG. 12D is a side view of yet another exemplary implantable microstimulator constructed in accordance with an embodiment of the present inventions.

It should be noted that, although the microstimulators described previously herein advantageously include elongate casings and electrode flaps that extend laterally, e.g., at an angle of about 30 to 150 degrees, relative to the longitudinal axis of the casing, other microstimulator configurations are also contemplated within the scope of the present inventions. For example, the electrodes 116 and electrode flaps 126 may extend parallel to the longitudinal axis 117 of the elongate casing 115. As shown in FIG. 12A, a microstimulator 1214A includes electrode flaps 126 that are attached directly to the lateral end surfaces 121 of the casing 115 such that the flaps 126 extend parallel to the longitudinal axis 117. As shown in FIG. 12B, a microstimulator 1214B includes an electrode flap 126 that is coupled directly to one of the lateral end surfaces 121 of the casing 115 such that the electrodes 116 extend substantially parallel relative to the longitudinal axis 117 of the casing 115. The flap 126 in FIG. 12B has a coiled or spiraled configuration. As shown in FIG. 12C, a microstimulator 1214C includes an electrode flap 126 with a curved configuration that is attached to one of the planar surfaces 123 of the casing 115 such that the electrodes 116 extend substantially parallel relative to the longitudinal axis 117 of the casing 115. As shown in FIG. 12D, a microstimulator 1214D includes electrode flaps 126 with curved configurations that are attached to one of the planar surfaces 123 of the casing 115 such that the flaps 126 overlap and the electrodes 116 extend substantially parallel relative to the longitudinal axis 117 of the casing 115.

Figure 12E:
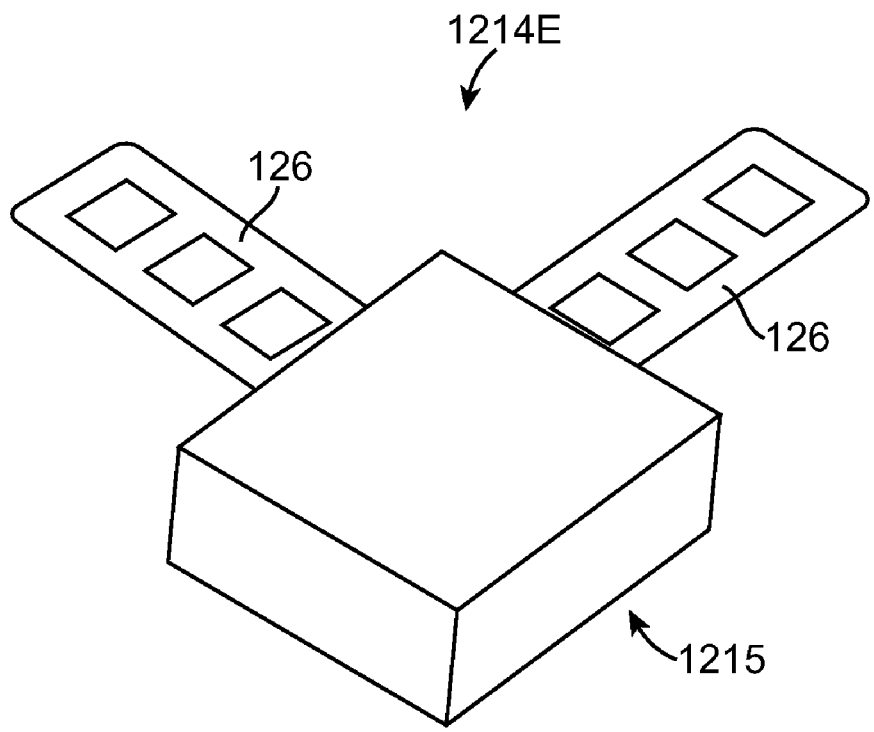
FIG. 12E is a perspective view of still another exemplary implantable microstimulator constructed in accordance with an embodiment of the present inventions.

In other alternative microstimulator configurations, rather than having an elongate casing with a longitudinal axis, the microstimulator casing may be square-shaped. For example, as shown in FIG. 12E, a microstimulator 1214E includes a square-shaped casing 1215 with electrode flaps 126 directly attached to two sides of the casing 1215.

Although particular embodiments of the present inventions have been shown and described, it will be understood that it is not intended to limit the present inventions to the preferred embodiments, and it will be obvious to those skilled in the art that various changes and modifications may be made without departing from the spirit and scope of the present inventions. Thus, the present inventions are intended to cover alternatives, modifications, and equivalents, which may be included within the spirit and scope of the present inventions as defined by the claims.

What is claimed is:

1. An implantable stimulator comprising:
a casing having an interior cavity;
stimulation circuitry housed in the interior cavity of the casing;
a flap coupled directly to the casing, wherein the flap is implantable in a flat configuration; and
one or more electrodes disposed on the flap.

2. The stimulator of claim 1, wherein the casing is an elongate casing having a longitudinal axis, and the one or more electrodes extend laterally relative to the longitudinal axis of the casing.

3. The stimulator of claim 2, wherein the one or more electrodes extend laterally at an angle between 30 and 150 degrees relative to the longitudinal axis of the casing.

4. The stimulator of claim 2, wherein the one or more electrodes extend substantially perpendicularly relative to the longitudinal axis of the casing.

5. The stimulator of claim 1, wherein the casing is an elongate casing have a longitudinal axis, and the one or more electrodes extend parallel relative to the longitudinal axis of the casing.

6. The stimulator of claim 1, wherein the flap comprises two lateral end edges, two longitudinal side edges, and two planar surfaces, and wherein one of the edges of the flap is coupled directly to the casing.

7. The stimulator of claim 1, wherein the flap comprises two lateral end edges, two longitudinal side edges, and two planar surfaces, and wherein one of the planar surfaces of the flap is coupled directly to the casing.

8. The stimulator of claim 1, wherein the one or more electrodes comprise a single elongated anode and a plurality of cathodes adjacent to the anode.

9. The stimulator of claim 1, wherein the one or more electrodes comprise two elongated anodes and a plurality of cathodes positioned between the anodes.

10. The stimulator of claim 1, further comprising:
another flap directly coupled to the casing; and
another one or more electrodes disposed on the other flap.

11. A method for performing a medical procedure on a patient using a microstimulator having a stimulation circuitry casing, a flap coupled directly to the casing, and electrodes disposed on the flap, the method comprising:
implanting the microstimulator in the patient with the flap in a flat configuration, such that the electrodes extend laterally over a target nerve; and
operating the microstimulator to apply stimulation to the target nerve.

12. The method of claim 11, wherein the implanting the microstimulator comprises positioning the casing substantially parallel to the target nerve.

13. The method of claim 11, wherein the implanting the microstimulator comprises positioning the casing substantially perpendicular to the target nerve.

14. The method of claim 11, wherein the implanting the microstimulator comprises positioning the casing at an angle of between 30 and 150 degrees relative to the target nerve.

15. An implantable stimulator comprising:
a casing having an interior cavity;
stimulation circuitry housed in the interior cavity of the casing;
one or more electrodes coupled to the stimulation circuitry for generating an electric field; and
a flap coupled directly to the casing, wherein the flap is configured for shaping the electric field generated by the electrodes, and wherein the flap is implantable in a flat configuration.

16. The stimulator of claim 15, wherein the one or more electrodes are disposed on a surface of the casing.

17. An implantable stimulator comprising:
a casing having an interior cavity;
stimulation circuitry housed in the interior cavity of the casing;
an electrically insulative coating disposed on the casing;
an electrically insulative flap coupled to the casing, wherein the coating and the flap are contiguous, and wherein the flap is implantable in a flat configuration; and
one or more electrodes disposed on the flap.

18. The stimulator of claim 17, wherein the coating and the flap are composed of the same material.

19. The stimulator of claim 17, further comprising:
another flap coupled to the casing, wherein the coating and the other flap are contiguous; and
another one or more electrodes disposed on the other flap.

* * * * *